US007667838B2

(12) United States Patent
Ackerman et al.

(10) Patent No.: US 7,667,838 B2
(45) Date of Patent: Feb. 23, 2010

(54) IN-STREAM SPECTROSCOPIC ELEMENTAL ANALYSIS OF PARTICLES BEING CONDUCTED WITHIN A GASEOUS STREAM

(75) Inventors: Richard Edgar Ackerman, San Diego, CA (US); Eric R. Empey, San Diego, CA (US); James Peter Stronski, San Diego, CA (US)

(73) Assignee: Thermo Gamma-Metrics LLC, San Diego, CA (US)

( * ) Notice: Subject to any disclaimer, the term of this patent is extended or adjusted under 35 U.S.C. 154(b) by 187 days.

(21) Appl. No.: 11/922,252

(22) PCT Filed: Jun. 16, 2006

(86) PCT No.: PCT/US2006/023598

§ 371 (c)(1),
(2), (4) Date: Dec. 14, 2007

(87) PCT Pub. No.: WO2006/138632

PCT Pub. Date: Dec. 28, 2006

(65) Prior Publication Data

US 2009/0040505 A1 Feb. 12, 2009

Related U.S. Application Data

(60) Provisional application No. 60/691,076, filed on Jun. 16, 2005.

(51) Int. Cl.
*G01N 15/02* (2006.01)

(52) U.S. Cl. .................. 356/335; 356/417; 356/246

(58) Field of Classification Search .............. 356/243.2, 356/244, 246, 417
See application file for complete search history.

(56) References Cited

U.S. PATENT DOCUMENTS

| 3,583,817 | A | * | 6/1971 | Rachlis et al. ............... 356/410 |
| 3,941,479 | A | * | 3/1976 | Whitehead ................... 356/335 |
| 6,211,956 | B1 | * | 4/2001 | Nicoli ......................... 356/337 |
| 6,482,652 | B2 | * | 11/2002 | Furlong et al. ................ 436/63 |

FOREIGN PATENT DOCUMENTS

CN  1501999 A  6/2004

* cited by examiner

*Primary Examiner*—Roy Punnoose
(74) *Attorney, Agent, or Firm*—Edward W. Callan

(57) ABSTRACT

A particle presentation apparatus for presenting particles being conducted within a gaseous stream for instream spectroscopic elemental analysis includes a particle blending section for homogenizing the distribution particles of significantly different sizes received within a gaseous stream of randomly distributed particles; and a particle sampling section including a window that is adapted for passing a particle excitation beam, such as a laser beam, and photon emissions, and a conduit for conducting the homogenized stream of particles past the window so that a particle excitation beam passing through the window can pass into the stream of homogenized particles. The apparatus may be used in combination with a drilling machine, wherein the particle blending section is coupled to an outlet pipe of the drilling machine for receiving a said gaseous stream of randomly distributed particles that are expelled from a drill hole.

14 Claims, 3 Drawing Sheets

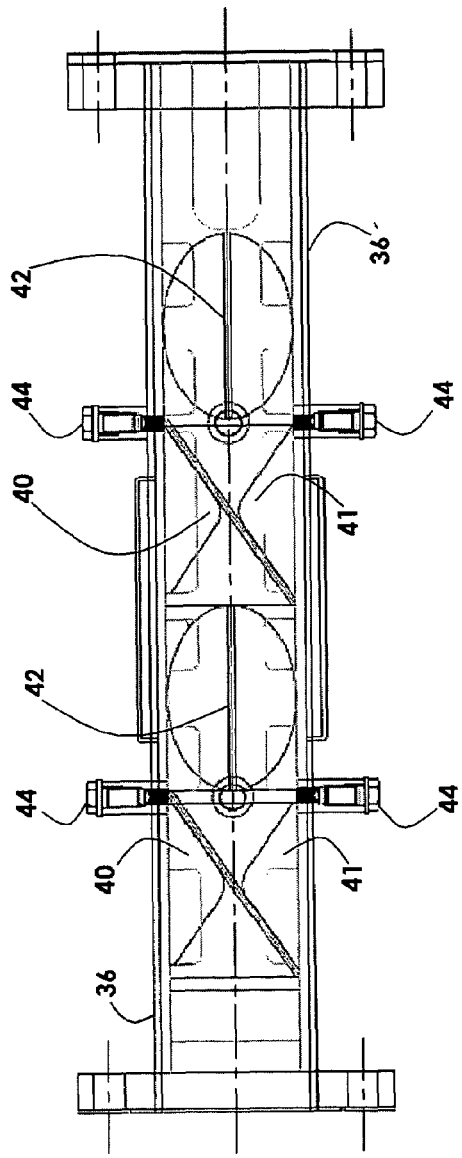
Fig. 3
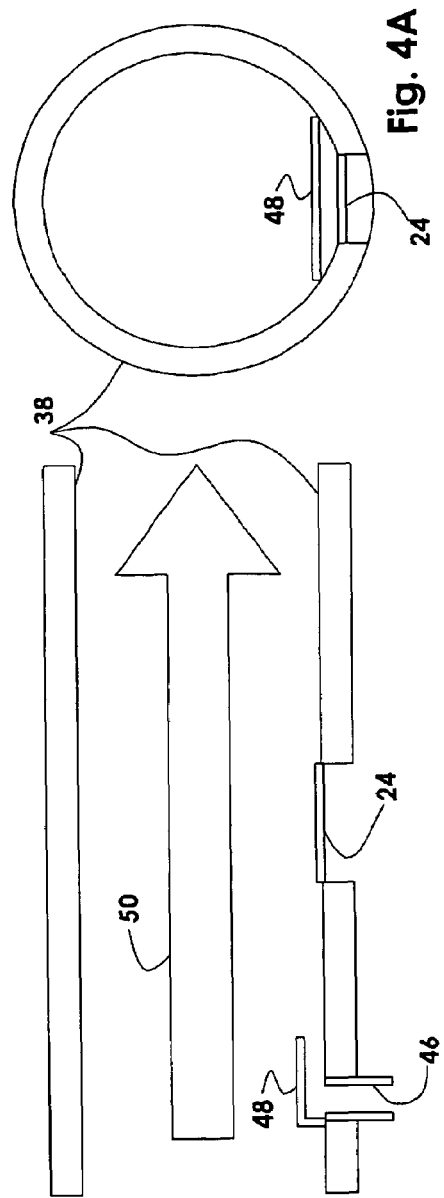
Fig. 4
Fig. 4A though the measurement volume during each sampling interval better approximates the average size of the particulate material within the entire gaseous stream, and thereby reduces the incidence of sampled measurements that are biased by random variations in the distribution of different size particles.

Additional features of the present invention are set forth in the detailed description.

IN-STREAM SPECTROSCOPIC ELEMENTAL ANALYSIS OF PARTICLES BEING CONDUCTED WITHIN A GASEOUS STREAM

CROSS-REFERENCE TO RELATED APPLICATION

This is a continuation-in-part of U.S. Provisional Patent Application No. 60/691,076 filed Jun. 16, 2005.

BACKGROUND AND SUMMARY OF THE INVENTION

The present invention generally pertains to elemental analysis of particulate matter and is particularly directed to in-stream spectroscopic elemental analysis of particles being conducted within a gaseous stream.

In many instances there is a significant randomness in the distribution of particulate matter that is being conducted within a gaseous stream for in-stream spectroscopic elemental analysis. Such randomness is caused by variations in particle size or weight, velocity profile in the gaseous stream, or flow geometry. The sizes of the particles in the gaseous stream may range from sub-micron to over 50 mm.

The present invention provides a particle presentation apparatus for presenting particles being conducted within a gaseous stream for in-stream spectroscopic elemental analysis, the apparatus comprising: a particle blending section for homogenizing the distribution of particles of significantly different sizes received within a gaseous stream of randomly distributed particles; and a particle sampling section including a window that is adapted for passing a particle excitation beam and photon emissions, and a conduit for conducting the homogenized stream of particles past the window so that a particle excitation beam passing through the window can pass into the stream of homogenized particles.

The present invention also provides a method of presenting particles for in-stream spectroscopic elemental analysis of particles of significantly different sizes received within a gaseous stream of randomly distributed particles, comprising the steps of:

(a) homogenizing the distribution of particles of significantly different sizes received within a gaseous stream of randomly distributed particles;

(b) conducting the homogenized stream of particles past a window that is adapted for passing a particle excitation beam and photon emissions, (c) emitting a particle excitation beam through the window and into the homogenized stream of particles being conducted past the window to thereby excite some of the particles within the stream, from which photons having wavelengths that are characteristic of the constituent elements or molecules of the particles are emitted through the window; and (d) communicating the emitted photons that pass through the window to a spectrometer.

Preferably, the particle excitation beam is a laser beam.

The present invention is particularly useful for in-stream elemental analysis by breakdown spectroscopy. Breakdown spectroscopy involves the creation of high temperature plasma which causes particle dissociation (break down). Electronic transitions in the atoms during the cooling of the plasma result in the emission of photons of characteristic wavelengths. Breakdown is commonly induced by laser, electric spark or microwave.

Breakdown spectroscopy produces a very small sensitive volume, with emission volumes on the order of 1 mm$^3$. Because of this, the measurement volume is often significantly smaller than the scale of the instantaneous variability in particulate material distribution in a received gaseous stream, and is often smaller than the maximum particle size. By homogenizing the distribution of the particles within the gaseous stream, the present invention presents the particles for breakdown and resultant spectral analysis in such a manner that the average size of the particulate material that is passing through the measurement volume during each sampling interval better approximates the average size of the particulate material within the entire gaseous stream, and thereby reduces the incidence of sampled measurements that are biased by random variations in the distribution of different size particles.

Additional features of the present invention are set forth in the detailed description.

BRIEF DESCRIPTION OF THE DRAWING

FIG. 3 is a sectional view of one embodiment of the particle blending section included in the particle presentation apparatus shown in FIG. 2.

FIG. 4 is a sectional view of one embodiment of the static mixer in the particle sampling section included in the particle presentation apparatus shown in FIG. 2.

FIG. 4A is a sectional end view of the particle sampling section shown in FIG. 4.

DETAILED DESCRIPTION

Figure 1:
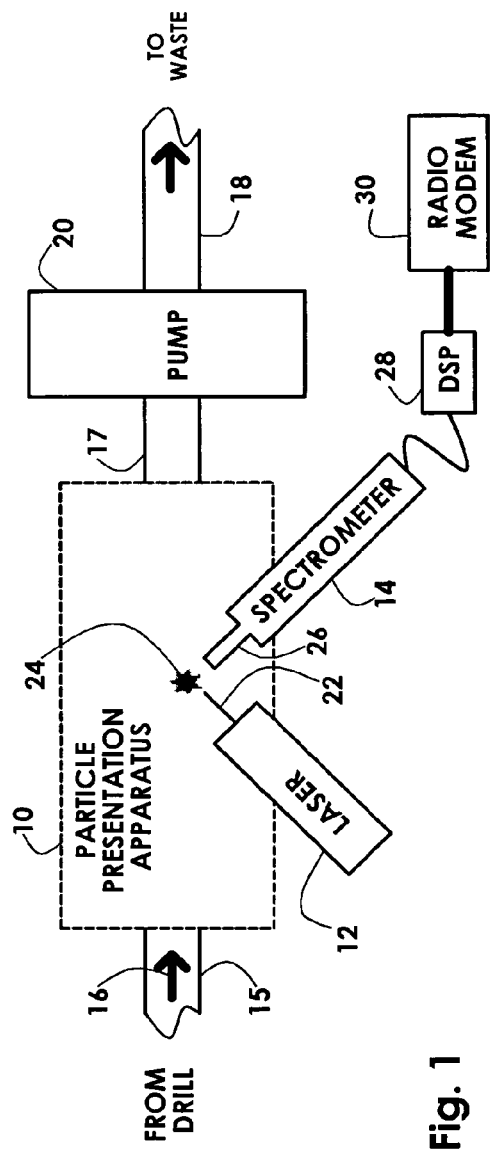
FIG. 1 is a diagram illustrating the utilization of a particle presentation apparatus according to the present invention in a system for performing elemental analysis by laser-induced breakdown spectroscopy.

Referring to FIG. 1, a particle presentation apparatus 10 according to one embodiment of the present invention is combined with a laser 12 and a spectrometer 14 in a system for performing elemental analysis by laser-induced breakdown spectroscopy (LIBS).

In one such embodiment the apparatus 10 is utilized for presenting particles that are contained within a gaseous stream that is expelled under pressure from a drill hole, whereby the apparatus 10 is mounted onto a drilling machine. The drilling machine includes an outlet pipe from which particles of earthen material loosened by the drill, but not brought to the surface by the drill, are expelled under pressure from the drill hole within a gaseous stream and ordinarily conducted through a system of pipes and/or hoses to a waste site. In this embodiment, the particle presentation apparatus 10 is coupled by a pipe and/or hose 15 to an outlet pipe (not shown) of the drilling machine for receiving the expelled gaseous stream of particles. Typically, the distribution of particles contained within such a gaseous stream includes particles of micrometer to millimeter size. This embodiment is particularly useful when the particles to be analyzed are extracted from a quarry.

The particle presentation apparatus 10 is coupled by a pipe and/or hose 15 to an outlet pipe (not shown) of a drilling machine from which particles of earthen matter loosened by the drill, but not brought to the surface by the drill, are expelled under pressure from the drill hole within a gaseous stream. The stream of particles is conducted through the particle presentation apparatus 10 in the direction shown by the arrows 16 and thence through a system of pipes and/or hoses 17, 18 to a waste site (not shown). When the velocity of the stream of particles is inadequate to propel the particles through the particle presentation apparatus 10 in an approximately collimated stream, a pump 20 is coupled to the system of waste disposal pipes and/or hoses 17, 18 to increase the velocity of the stream of particles so that the stream is approximately collimated.

The laser 12 emits a laser beam 22 through a window 24 in the particle presentation apparatus 10 and thence into the stream of particles in order to create plasma that induces the breakdown or fluorescence of the particles. Photons emitted from the event pass through the window 24 from within the particle presentation apparatus 10 and thence through an optical system 26 to the spectrometer 14. In some embodiments, the window 24 is an optical lens.

The particle presentation apparatus 10, laser 12, the spectrometer 14 and the optical system 26 are designed to withstand vibration and shock in order to maintain optical performance while being used in the environment of the drilling machine. Instrumentation (not shown) is coupled to a drill depth gauge in order to transmit elemental analysis as a function of drill depth. This analysis is combined with location data received from a GPS system when the drill is repositioned to thereby provide three-dimensional mapping of rock quality within a quarry.

Laser power is selected to create a stable plasma of sufficient size to produce an adequate signal in the spectrometer. Laser power also contributes to the evolution of plasma temperature, which impacts the relative intensity of spectral lines. Thus, signal-to-noise is impacted by the selection of laser power.

Variation of the gate delay for the spectrometer (the time between the laser pulse and start of the spectrometer collection) changes the amount of continuum light emitted from the plasma that is collected by the spectrometer and also changes the relative line intensities in the spectrum, as the plasma cools and high energy excitation levels decay.

In the preferred embodiments, spectra are collected using different spectrometer gate delays to determine the optimal signal-to-background ratio for respectively different elements. Longer gate delays allow for the decay for the broadband plasma radiation (background), but also result in the loss of signal as well. Longer gate delays appear to be best from a signal-to-background ratio perspective.

The spectrometer is selected for sensitivity, resolution, and timing. In one embodiment, a non-intensified CCD based spectrometer is used. A single spectrometer is the simplest and least expensive solution for spectra collection, but resolution is typically limited to 2000 to 4000 pixels, which must cover the wavelengths of the emitted photons of interest, generally in the range of approximately 200 to 900 nm. Using an additional spectrometer can improve resolution, but also adds cost and complexity. The integration time for the spectrometer should be short enough to avoid changes in the signal caused by cooling the plasma and to enable spectra to be collected for different gate delays while avoiding such changes.

Figure 2:
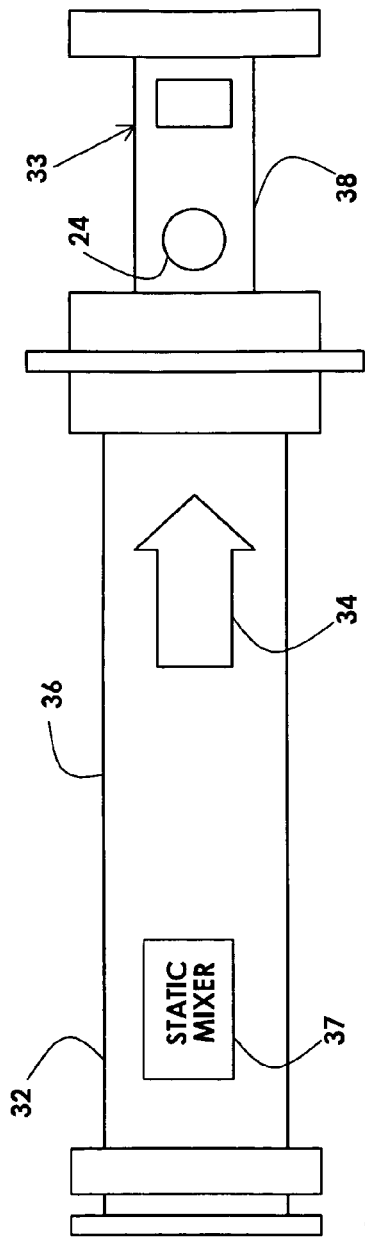
FIG. 2 is a diagram of a preferred embodiment of a particle presentation apparatus according to the present invention.

A digital signal processor 28 is coupled to the spectrometer 14 for processing the spectrometer output signals. A radio modem 30 is coupled to the digital signal processor 28 for transmitting the processed spectrometer output signals to a location that is remote from the drilling site Referring to FIG. 2, one embodiment of the particle presentation apparatus 10 includes a particle blending section 32 and a particle sampling section 33. The stream of particles is conducted through both sections 32, 33 in the direction shown by the arrow 34. The orientation of the flow of the stream of particles through the particle presentation apparatus 10 is horizontal in the preferred embodiment. Such orientation may be otherwise in other embodiments.

The particle blending section 32 includes a conduit 36 for conducting the stream of particles and a static mixer 37 for blending the particles within the stream of particles received within the conduit 36 from the pipe 15 to thereby enhance the uniformity of distribution of different size and mass particles within the stream of particles that is conducted through the particle sampling section 33. The particle sampling section 33 includes a conduit 38 for conducting the stream of particles and the window 24 for enabling the laser beam 22 and the emitted photons to pass though the wall of the conduit 38.

Referring to FIG. 3, one embodiment the static mixer 37 of the particle blending section 32 includes repeating series of differently shaped baffles 40, 41, 42 for blending the particles. The baffles are mounted to the conduit 36 by screws 44. The baffles 40, 41, 42 are disposed at different angles with respect to one another. In the preferred embodiment, the particle blending section 32 is a product identified by ASX80-4-S4-NRL-A150 that is sold by PACT International PTY LTD of Australia. The baffles 40, 41, 42 are removable and replaceable. The baffles must be replaced from time to time because of wear resulting from contact with the stream of particles.

In an alternative embodiment (not shown), the static mixer 37 includes a system of nozzles that are disposed for enhancing the uniformity of distribution of different sized particles within the stream of particles. In other embodiments (not shown), the means for enhancing the uniformity of distribution of different sized particles within the stream of particles is other than a static mixer.

Referring to FIGS. 4 and 4A, the particle sampling section 33 includes the window 24, an inlet 46 through the wall of the conduit 38 through which a jet of gas is pumped under high pressure from an external source (not shown) and a baffle 48 for directing the injected jet of air past the interior surface of the window 24 in a direction parallel to the flow of the stream of particles, as indicated by the arrow 50. The baffle 48 causes the jet of air to be relatively flat while moving past the interior surface of the window 24. The jet of air is pumped past the interior surface of the window 24 at a much higher velocity than the velocity of the stream of particles.

Contact against the window 24 by the particles within the stream is diminished by directing the relatively higher velocity jet of clean air past the interior surface of the window 24. Diminishing contact against the window 24 by the particles within the stream thereby diminishes damage to the window 24 and reduces any obscuring of the laser beam 24 and of the photon emissions that result from a buildup of fine particles on the interior surface of the window 24. The window 24 should be kept clean and unscratched in the presence of fine and/or abrasive powders, because build-up or clouding of the window will absorb laser power and degrade the plasma or burn the window and prevent light transmission. 70 mJ is sufficient energy to cause burning of material on the window 24 if the window 24 is not actively kept clean.

An air curtain also has been used, wherein the air flow is laminar across the face of the window 24 and parallel to the process stream. A transverse laminar air curtain also can be used.

In alternative embodiments (not shown), (a) the jet of air is directed against the window 24; (b) the jet of air is directed in a direction other than parallel to the flow of the stream of particles; and/or (c) the velocity of the jet of air is not much higher than the velocity of the stream of particles.

A shutter (not shown) is incorporated within the conduit 38 to keep the window 24 clear in case of a loss of the air flow, significant reduction of air flow pressure, or water ingress. In the preferred embodiment, the shutter is a sealed slide valve, actuated by a spring loaded pneumatic cylinder. The preferred pressure of the air flow holds the cylinder open against the spring restoring force. Loss of the air flow or significant reduction of air flow pressure causes the spring to close the shutter by sealing the valve. The shutter system is interlocked to the control electronics of the spectral analysis system so that air flow must be enabled before the shutter will open. Detection of moisture in the air flow stream that is being provided to the inlet 46 also will cause the shutter to close. The laser is interlocked to the shutter so that it will not fire until the shutter is opened. The shutter can be electrically or mechanically actuated as well.

Laser beam delivery and photon collection may share the same optical axis or maintain unique axes. Coaxial arrangements must separate the delivered laser beam and the collected photons at some point. This may be done by turning the laser beam, the collected photons, or both from the primary optical axis. The laser beam may be turned by 90 degrees by using a mirrored right angle prism. Alternately, any laser-grade mirror or prism could be used, including dielectric or dichroic materials. By contrast, the optics could be oriented so that the optical axis of the focusing and collecting lenses is the same as the primary laser axis, while the collected photons are turned off axis by use of some mirror arrangement (pierced mirrors, dichroic, or dielectric mirrors are options).

The nature of dust and particle transport is such that optical density along the focusing path of the laser beam is variable. As such, the location of breakdown or fluorescence by the laser beam is not fixed along its path to the exact focus of the lens, but rather varies by several millimeters. The optical design must therefore be such that variation in object location does not significant impact photon collection. For this reason, in one embodiment the laser beam delivery and photon collection optics are designed to share the same optical path through the window 24. Alternatively, laser beam delivery and photon collection may utilize independent optical paths, with the photon collection being oriented at any angle to the delivered laser beam. Transverse (90 degree) orientation is an obvious alternative.

Collected photons are captured by a linear CCD based spectrometer, where they are processed into a spectrum and transmitted to a remote computer for analysis. Photon collection is accomplished by using several different types of spectrometers, including CCDs, intensified CCDs, and photomultiplier tube arrays (PMTs).

Figure 5:
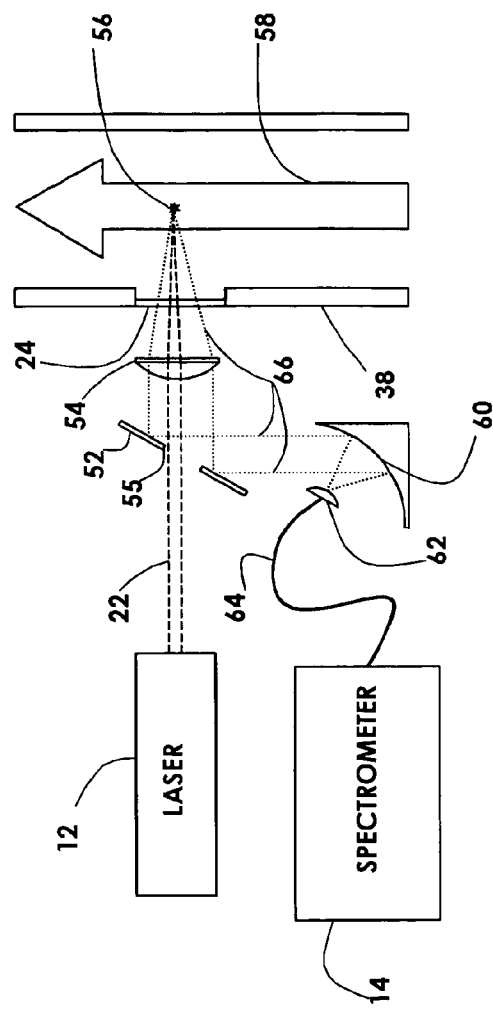
FIG. 5 is a diagram illustrating of one embodiment of an optical systems by which a laser and a spectrometer are combined with the particle presentation apparatus of FIG. 2 for performing elemental analysis by laser-induced breakdown spectroscopy.

Referring to FIG. 5, in one embodiment, the laser 12 is coupled to the particle sampling section 33 of the particle presentation apparatus 10 by an optical system that includes a pierced mirror 52 and a laser focusing lens 54. The laser beam 22 passes through an aperture 55 in the center of the pierced mirror 52, the laser focusing lens 54 and the window 24 to induce a plasma 56 in the stream of particles that is being conducted through the conduit 38 in the direction shown by the arrow 58. For simplicity of illustration, the inlet 46 and the plate 48 are omitted from FIG. 5.

The spectrometer 14 is coupled to the particle sampling section 33 of the particle presentation apparatus 10 by an optical system that includes the laser focusing lens 54, the pierced mirror 52, a parabolic mirror 60, an optical fiber lens 62 and an optical fiber 64 that is coupled to the optical fiber lens 62. The photons 66 emitted from the disassociated particles during the cooling of the plasma 56 pass through the window 24 and the laser focusing lens 54, are reflected by the pierced mirror 52 onto the parabolic mirror 60, and reflected by the parabolic mirror 60 to the optical fiber lens 62, which passes the emitted photons to the optical fiber 64 for conduction to the spectrometer 14.

The position of the breakdown of the particles in the plasma is variable, particularly when there is a low particle density within the conduit 38. Accordingly, it is preferred that the spectrometer 14 not be finely focused on a small region, but rather be able to view several millimeters along the axis of the laser beam 22.

The optical fiber 64 has a limited diameter and acceptance angle; and the parabolic mirror 60 may not perfectly focus the light. In order to increase the effective size of the viewable image, and to improve the effective acceptance angle of the optical fiber 64 a ball lens is preferred as the optical fiber lens 62, whereby the spectrum of the collected emission is less sensitive to positioning of the laser 12 and the optical systems in relation to the plasma 56.

Figure 6:
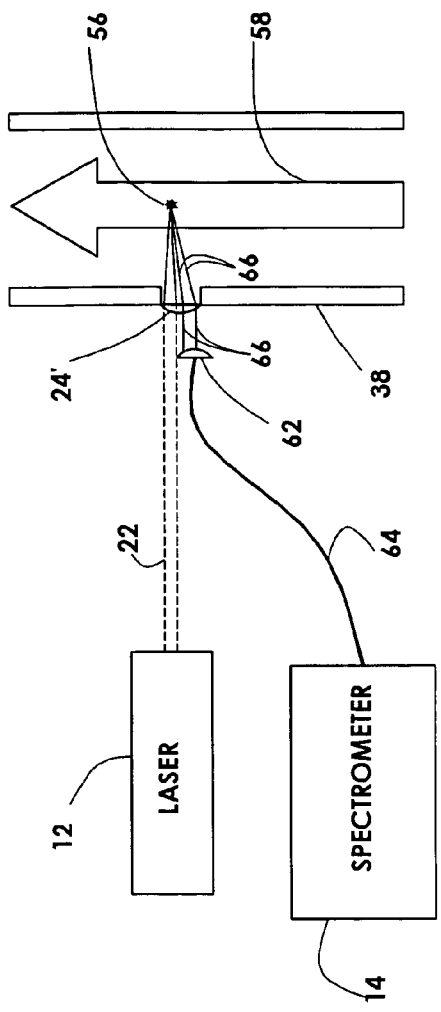
FIG. 6 is a diagram illustrating of another embodiment of an optical systems by which a laser and a spectrometer are combined with the particle presentation apparatus of FIG. 2 for performing elemental analysis by laser-induced breakdown spectroscopy.

Referring to FIG. 6, in another embodiment, the laser 12 is coupled to the particle sampling section 33 of the particle presentation apparatus 10 by an optical system that includes a laser focusing lens 24' that also functions as the window 24' in the conduit 38 of the particle sampling section 33. The laser beam 22 passes through the laser focusing lens/window 24' to induce plasma 56 in the stream of particles that is being conducted through the conduit 38 in the direction shown by the arrow 58. For simplicity of illustration, the inlet 46 and the plate 48 are omitted from FIG. 6.

The spectrometer 14 is coupled to the particle sampling section 33 of the particle presentation apparatus 10 by an optical system that includes the laser focusing lens/window 24', an optical fiber lens 62 and an optical fiber 64 that is coupled to the optical fiber lens 62. The photons 66 emitted from the particles within the plasma 56 pass through the laser focusing lens/window 24' to the optical fiber lens 62, which passes the emitted photons to the optical fiber 64 for conduction to the spectrometer 14. Although the light collection provided by the optical systems shown in the embodiment of FIG. 6 is not as light-efficient as the light collection provided by the optical systems shown in the embodiment of FIG. 5, the optical systems shown in the embodiment of FIG. 6 are much more robust and provide more light than needed for many applications.

For some embodiments (not shown), sensitivity to relative positioning of the laser 12 and the optical systems in relation to the plasma 56 is decreased by eliminating most of the optical components, particularly the mirrors, and by using fiber optics where possible. In one such embodiment a fiber delivers the laser to a focusing window in the conduit of the particle sampling section. The spectrometer is also fiber coupled to the window, and a collecting lens is used.

In other aspects, the methods and apparatus of the present invention are utilized for in-stream elemental analysis by alternative spectroscopic analysis techniques that do not utilize breakdown spectroscopy. One such alternative technique utilizes fluorescent spectroscopy.

A vertical orientation of the flow of the stream of particles is used when analyzing material sampled from a calciner. The sampler from the calciner expels the sample by gravity and the sample falls directly through the sampling section of the particle presentation apparatus.

In other embodiments, the present invention is utilized for presenting particles for elemental analysis by spectroscopy, wherein the particles are contained within a stream of raw meal, hot meal (material extracted from a calciner that is at ≈1000° C.), fly ash (a component added to the raw meal), cement (finished product), stack gas (analyze pollutants), pulverized coal, sinter, or by-pass dust or kiln dust (exhaust from a pre-heater).

In some embodiments, the particles are not contained within a gaseous stream that is propelled under pressure. For example, the particles are contained within a stream that is propelled by gravity.

The present invention is useful in the cement industry and in the mineral and metals industries wherein raw materials are quarried or mined. In many processes, the raw materials and process additives are milled to produce particles of μm to mm size. All of these materials can be analyzed by breakdown spectroscopy or a variant thereof.

In the preferred embodiments, particle breakdown is induced by laser beams. In other embodiments particle breakdown is induced by other means, such as electric sparks or microwaves.

The particle presentation apparatus of the present invention is mobile. Though it can be mounted at a fixed location, it is possible to readily transport the particle presentation apparatus for mobile diagnostics.

The benefits specifically stated herein do not necessarily apply to every conceivable embodiment of the present invention. Further, such stated benefits of the present invention are only examples and should not be construed as the only benefits of the present invention.

While the above description contains many specificities, these should not be construed as limitations on the scope of the present invention, but rather as examples of the preferred embodiments described herein. Other variations are possible and the scope of the present invention should be determined not by the embodiments described herein but rather by the claims and their legal equivalents.

The invention claimed is:

1. A particle presentation apparatus for presenting particles being conducted within a gaseous stream for in-stream spectroscopic elemental analysis, the apparatus comprising:
    a particle blending section for homogenizing the distribution of particles of significantly different sizes received within a gaseous stream of randomly distributed particles; and
    a particle sampling section including a window that is adapted for passing a particle excitation beam and photon emissions, and a conduit for conducting the homogenized stream of particles past the window so that a particle excitation beam passing through the window can pass into the stream of homogenized particles.

2. An apparatus according to claim 1 in combination with a drilling machine, wherein the particle blending section is coupled to an outlet pipe of the drilling machine for receiving a said gaseous stream of randomly distributed particles that are expelled from a drill hole.

3. An apparatus according to claim 1, wherein the window is a focusing lens.

4. An apparatus according to claim 1, further comprising:
    means for diminishing contact against the window by the particles within the stream in order to diminish damage to the window.

5. An apparatus according to claim 4, wherein the means for diminishing contact includes means for directing a jet of clean air past or against the interior surface of the window.

6. An apparatus according to claim 5, wherein the means for diminishing contact includes a shutter incorporated within the conduit to keep the window clear in case of a loss of the air flow, significant reduction of air flow pressure, or water ingress.

7. An apparatus according to claim 6, wherein the shutter is a sealed slide valve that is actuated by a spring loaded pneumatic cylinder.

8. An apparatus according to claim 7, wherein the preferred pressure of the air flow holds the shutter open against the spring restoring force and loss of the air flow or significant reduction of air flow pressure causes the spring to close the shutter by sealing the valve.

9. An apparatus according to claim 6, wherein the particle excitation beam is interlocked to the shutter so that the beam will not fire until the shutter is opened.

10. An apparatus according to claim 1 in combination with means for propelling the gaseous stream under pressure or gravity through the particle blending section and the particle sampling section.

11. A method of presenting particles for in-stream spectroscopic elemental analysis of particles of significantly different sizes received within a gaseous stream of randomly distributed particles, comprising the steps of:
    (a) homogenizing the distribution of particles of significantly different sizes received within a gaseous stream of randomly distributed particles;
    (b) conducting the homogenized stream of particles past a window that is adapted for passing a particle excitation beam and photon emissions,
    (c) emitting a particle excitation beam through the window and into the homogenized stream of particles being conducted past the window to thereby excite some of the particles within the stream, from which photons having wavelengths that are characteristic of the constituent elements or molecules of the particles are emitted through the window; and
    (d) communicating the emitted photons that pass through the window to a spectrometer.

12. A method according to claim 11, further comprising the step of:
    (e) receiving the gaseous stream of randomly distributed particles that is homogenized pursuant to step (a) from a drill hole, wherein the particles are expelled from the drill hole.

13. A method according to claim 11, further comprising the step of:
    (e) diminishing contact against the window by the particles within the stream in order to diminish damage to the window.

14. A method according to claim 13, when step (f) comprises the step of:
    (f) directing a jet of clean air past or against the interior surface of the window.

* * * * *